United States Patent [19]
Hussman

[11] Patent Number: 6,135,993
[45] Date of Patent: Oct. 24, 2000

[54] OPTICAL LOCALIZATION FIBER

[76] Inventor: Karl L. Hussman, 81 Orange St., #FM301, New Haven, Conn. 06510

[21] Appl. No.: 08/423,077

[22] Filed: Apr. 17, 1995

[51] Int. Cl.⁷ ..................................................... A61N 5/06
[52] U.S. Cl. ................. 606/2; 606/10; 606/130; 606/167
[58] Field of Search ............................. 606/2, 3–18, 130, 606/167

[56] References Cited

U.S. PATENT DOCUMENTS 5,370,640  12/1994  Kolff .......................................... 606/2

*Primary Examiner*—David M. Shay
*Attorney, Agent, or Firm*—Timothy Thut Tyson Freilich, Hornbaker & Rosen

[57] ABSTRACT

An optical localization fiber 20 is provided suitable for preoperative localization of soft tissue lesions by x-ray mammography, CT, MRI, ultrasonography, or nuclear medicine. A hook 28 is carried by the optical fiber for retaining the fiber in soft tissue. The tip 26 of the optical fiber is visible through the soft tissue when the proximal end of the optical fiber is attached to a light source 170. Other embodiments include clad or coated 42 optical fibers, bundled optical fibers 156, hooks which are metallic 82, braided 66, and multiple 128, and a helix 162.

22 Claims, 3 Drawing Sheets

OPTICAL LOCALIZATION FIBER

TECHNICAL FIELD

The present invention relates generally to preoperative tissue localization apparatus and more particularly to preoperative breast localization by x-ray radiography, CT ultrasonography, nuclear medicine or magnetic resonance imaging (MRI).

BACKGROUND ART

The current state of the art of preoperative breast tumor localization requires the placement of either a metallic hookwire or a trail of medical grade powdered carbon suspension proximate to the tumor via a localization needle. In the former method, x-ray mammography, ultrasound, or magnetic resonance imaging is used to visualize the lesion in question. The breast is then fixed by compression means, non-compressive immobilization means, or, in the case of ultrasound, manually. A needle is inserted into the breast so that its tip lies proximate to the breast lesion. If carbon localization is used, a trail of carbon is formed from the lesion to the skin surface as the carbon suspension is injected through the needle as the needle is withdrawn. If hookwire localization is used, a fine metallic wire is inserted through the needle. The wire typically is bent or curved at the tip so that it forms a small hook. If the bend is sharp, the hook springs apart as it is passed distal to the tip of the localization needle. In this manner, it becomes substantially fixed at the site of the needle tip. The needle is then withdrawn leaving the hookwire in place. The patient is taken to surgery where the surgeon follows at least part of the carbon trail or hookwire to find the lesion for excision.

Copious references pertaining to the use of hook-wires in the imaging literature are available. Literature references include Gallagher, W. J., et al., "Minimal Volume Excision of Nonpalpable Breast Lesions," *American Journal of Radiology*, 152:957, 1989; Czarnecki, D. J., et al., "Toluidine Blue Dye as a Breast Localization Marker," *American Journal of Radiology*, 153:261, 1989; Schoenberger, S. G., et al., "New Coaxial Needle for Pre-operative Localization of Breast Abnormalities," *British Journal of Radiology*, 64:669, 1989; Langlois, S. L. P., Carter, M. L., "Carbon Localization of Impalpable Mammographic Abnormalities," *Australian Radiolocry*, 35:237, 1991; Czarnecki, D. J., et al., "Comparison of the Anchoring Strengths of the Kopans and Hawkins II Needle-hookwire Systems," *Radiology*, 183:573, 1992; D'Orsi, C. J., et al., "Complication Involving a Braided Hookwire Device," *Radiology*, 187:580, 1993; Ghiatas, A. A., et al., "Modified Localization Wire for Breast Lesions," *European Radiology* 2:266, 1992; Homer, M. J., et al., "Prebiopsy Needle Localization: Methods, Problems and Expected Results," *Radiological Clinics of North America*, 30:139, 1992; Homer, M. J., "Localization of Non-palpable Breast Lesions with the Curved-end, Retractable Wire," *American Journal of Radiology*, 151:919, 1989; Urritia, E. J., et al., "Retractable-barb Needle for Breast Lesion Localization," *Radiology*, 169:845, 1988. References pertaining to transillumination of breast tissue are: Jariman, O., "Time-resolved Transillumination of the Breast," *Acta Radiologica*, 33:228, 1992; and, Monsees, B., et al., "Light Scan Evaluation of Non-palpable Breast Lesions," *Radiology*, 167:352, 1987. A reference pertaining to optical fiber diffuser tips is Malone, D. E., et al., "Sonographic Changes During Hepatic Interstitial Laser Photocoagulation: an investigation of Three Optical Fiber Tips," *Investigative Radiology*, 27:804–813, 1992. The disclosures of the above cited references are hereby incorporated into and liberally drawn from for this background section.

Often the location of the hookwire tip is not readily apparent, and the surgeon must use measurements of the hookwire length, and visual triangulation to help guide him/her. A tugging maneuver is sometimes utilized in order to find the tip since the breast tissue will then move in the locality of the hookwire tip. This maneuver may displace the hookwire tip however. While it is possible to locate the tip of the hookwire fluoroscopically, this method requires a dedicated fluoroscopy suite and radiation protective aprons for all operating room personnel. In addition, unless the fluoroscopic tube can be angled to yield mediolateral and anteroposterior projections, the precise depth of the hookwire cannot be readily ascertained. For these reasons, fluoroscopic guidance is not feasible.

Intraoperative transillumination of the breast with an external light source has been used in conjunction with carbon localization for delineation of the dark carbon trail against the reddish glow of surrounding transilluminated breast tissue.

Both the hookwire and carbon trail methods are cumbersome in actual use. The tip of a hookwire cannot be seen through breast tissue, and the surgeon may have to search for it, commonly necessitating longer operating time, and a larger incision. A carbon trail tends to blacken surrounding tissue if it is cut into by a surgeon. Because of this, it is not always possible to determine the exact end of the trail. Commonly, the carbon trail may become broken if a steady stream of carbon is not injected. A method of localization that is easier to see and requires smaller incisions would offer many advantages.

DISCLOSURE OF INVENTION

The present invention is directed to an optical localization fiber with a hooked tip for preoperative localization of breast lesions identified by x-ray mammography, ultrasound, MRI, or nuclear medicine. The optical fiber enables the surgeon to identify the tip of the optical fiber by the light which preferably originates from a laser connected to the origin of the optical fiber.

The optical fiber has the advantage of allowing continuous and direct visualization of the light emanating through breast tissue from the fiber tip. Smaller breast incisions need be made and smaller amounts of tissue need be removed during breast surgery. In addition, the surgical approach to lesions need not be along the course of the localizing optical fiber, since radiant light emanating from the site of the lesion may be seen from any perspective.

Apparatus in accordance with the invention are characterized by an optical fiber of a diameter which allows passage through a localization needle, a hook or curve to allow retention in a breast substantially without displacement, and a tip which allows diffusion of transmitted light for visualization through breast tissue by the surgeon.

In a preferred embodiment the optical fiber is bare, without cladding and or/coating. Alternatively, the optical fiber is clad and/or coated. Either type of fiber may be bundled.

In another preferred embodiment the hook is formed by the optical fiber. Alternatively, the optical fiber is joined to a braided wire hook or the entire optical fiber shaft is joined to a longitudinal wire.

Other preferred embodiments include multiple hooks, a pincher hook, or a helix for retention of the optical fiber within tissue.

In other preferred embodiments, the optical localization fibers are staggered or form a rosette. All embodiments may be used in combination with carbon marking of the lesion site to facilitate visualization of the region to be surgically excised.

The novel features of the invention are set forth with particularity in the appended claims. The invention will best be understood from the following description when read in conjunction with the accompanying drawings.

BEST MODES FOR CARRYING OUT THE INVENTION

Figure 1:
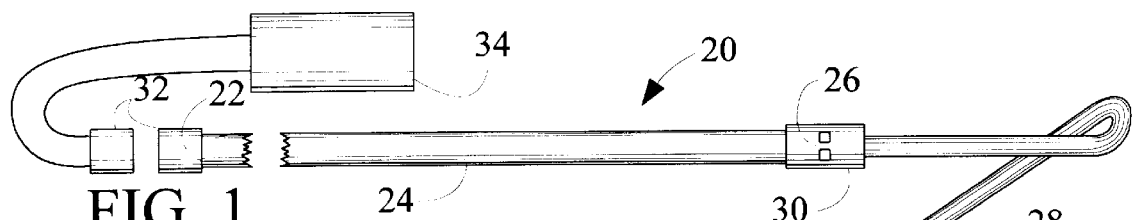
FIG. 1 is a side view of a diffusing optical localization fiber in accordance with the present invention.
Figure 11:
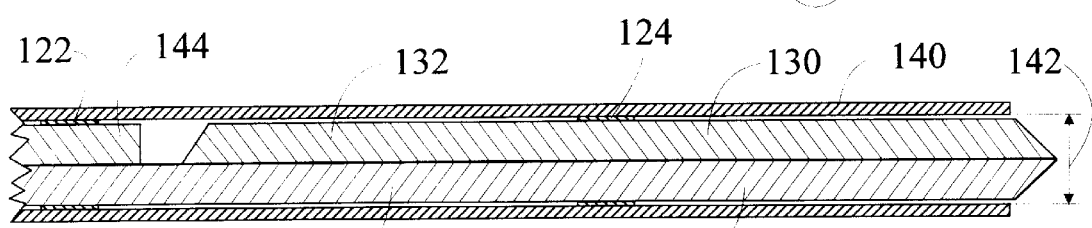
FIG. 11 is an enlarged cross sectional side view of a pincher hook optical localization fiber within a localization needle.

FIG. 1 illustrates a side view of a diffusing optical localization fiber 20 in accordance with the present invention having an origin 22, a shaft 24, and an optical fiber tip 26. A metallic or plastic hook 28 is bound to the tip by means of a connection 30. The hook has a spring action to engage in tissue once the localization needle is withdrawn. A sectional view of a localization needle with an optical fiber inside prior to insertion is shown in FIG. 11. Radiant light emanating from the localization fiber tip may be diffused by the connector 30 if it is made of a translucent material including plastic quartz and ground glass. Alternatively, the connector 30 may be opaque, but fenestrated to allow light to emanate from the optical fiber tip 26. A coupler 32 is located at the origin 22 of the diffusing optical localization fiber 20 to unite with a laser or other light source 34.

Figure 2:
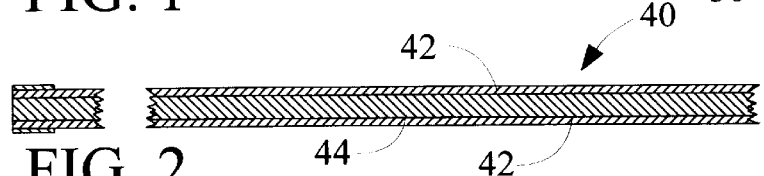
FIG. 2 is a longitudinal cross sectional view of an optical localization fiber with a cladding or coating.

FIG. 2 illustrates a longitudinal cross sectional view of an optical fiber 40 with cladding and/or coating 42 along the shaft 44.

Figure 3:
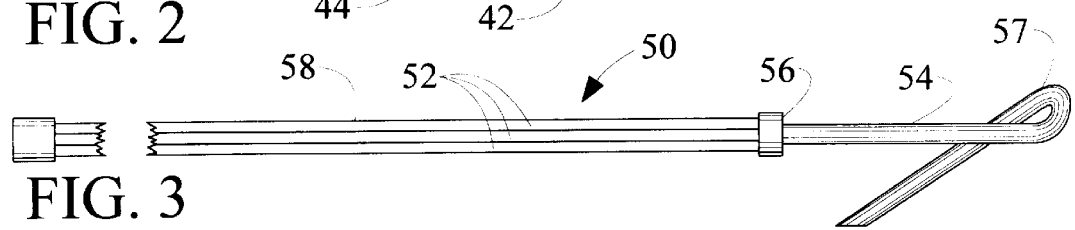
FIG. 3 is a side view of a bundled optical localization fiber.

FIG. 3 illustrates a bundled optical localization fiber 50 with individual fibers 52. A metal or plastic hook 54 is affixed to the tip of the fiber bundle and arises from a small metallic or plastic fastener 56 bound to the tip of the bundled optical localization fiber 50 either by adhesive, integration with the cladding and/or coating 58 (not shown here), or by a variety of other conceivable means. The hook 54 may have the form of a smooth curve or of a sharp bend 57 and may be fashioned from stainless steel including high nickel content stainless, titanium, nitinol, or a variety of other metals including those which cause low artifact during magnetic resonance imaging. Hooks with either a smooth curve or sharp bend have a spring action which allows them to be inserted through a localization needle such as the localization needle of FIG. 11. Both types of hooks snag tissue, preventing displacement when the localization needle is withdrawn. The bundled optical localization fiber 50 preferable has a diameter allowing insertion through a 14 through 22 gauge needle, although the preferred diameter is 20 gauge.

Figure 4:
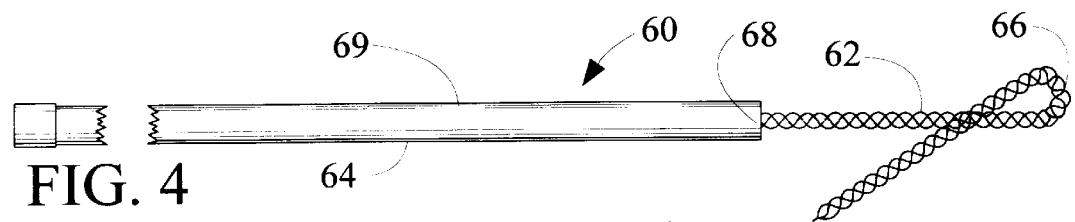
FIG. 4 is a side view of a hybrid optical localization fiber joined to a spiral wire along its shaft.

FIG. 4 illustrates a hybrid optical localization fiber 60 with a spiral metallic wire 62 extending down the shaft 64. The spiral metallic wire 62 forms a braided metallic hook 66 past the optical fiber tip 68. Cladding and/or coating 69 prevents unravelling of the spiral metallic wire.

Figure 5:
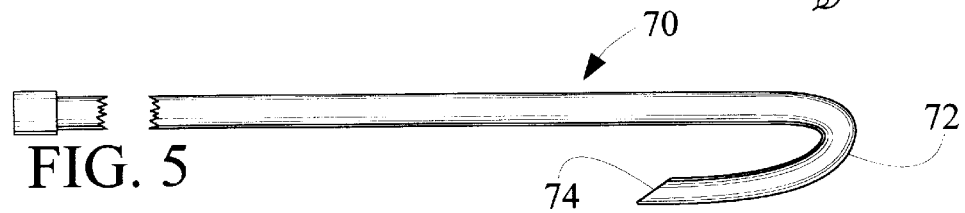
FIG. 5 is a side view of a single composition optical localization fiber.

FIG. 5 illustrates a single composition optical localization fiber 70. The optical fiber hook 72 is molded from the optical fiber itself, and is resilient allowing passage of the optical localization fiber 70 through a needle. The fiber 70 curves as the optical fiber tip 74 emerges from a needle. The bundled optical localization fiber 50 (FIG. 3) may be molded to form a similar curve. The optical fiber hook has a point to penetrate breast tissue and thereby facilitate retention.

Figure 6:
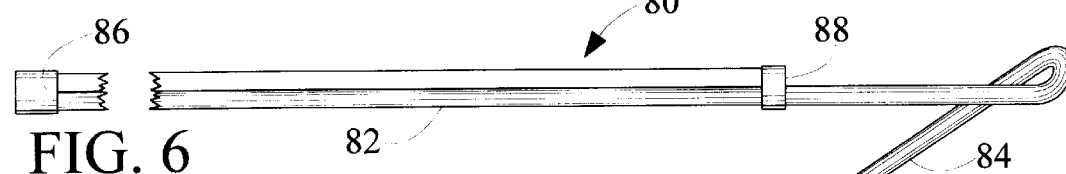
FIG. 6 is a side view of a tandem optical localization fiber.

FIG. 6 illustrates a tandem hookwire-optical localization fiber 80. A longitudinal wire 82 runs down the shaft of the fiber optical on the surface, totally beneath the surface, partially beneath the surface, outside a coating, inside a coating, on the surface of bundled optical fibers, or within bundled optical fibers. The longitudinal wire 82 is continuous with a metallic hook 84 and is held on the optical fiber or fibers 80 by fasteners 86 and 88.

Figure 7:
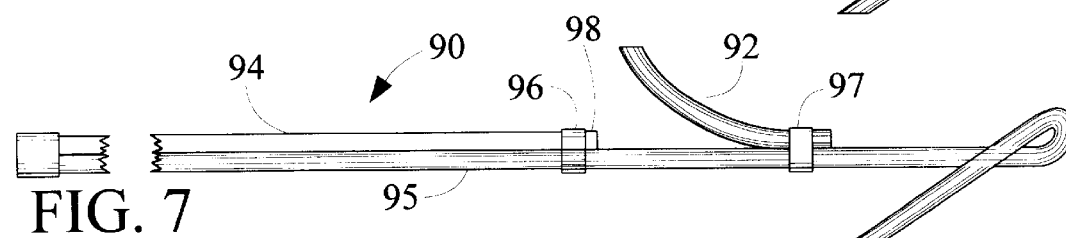
FIG. 7 is a side view of a multi-hook optical localization fiber.

FIG. 7 illustrates a multi-hook optical localization fiber 90. A variety of possible configurations, orientations, and positions of a plurality of hooks can readily be envisioned all of which are intended to be represented by this generic illustration. For example, a second hook 92 is shown. Since this hook and similar hooks are inside the combination of the diameters of the fiber optic 94 and combination longitudinal wire 95, no increase in needle diameter is necessary. The entire localization wire may be metallic without an optical fiber component. Fasteners 96 and 97 are positioned both at the optical fiber tip 98 and around the straight hook 92.

Figure 8:
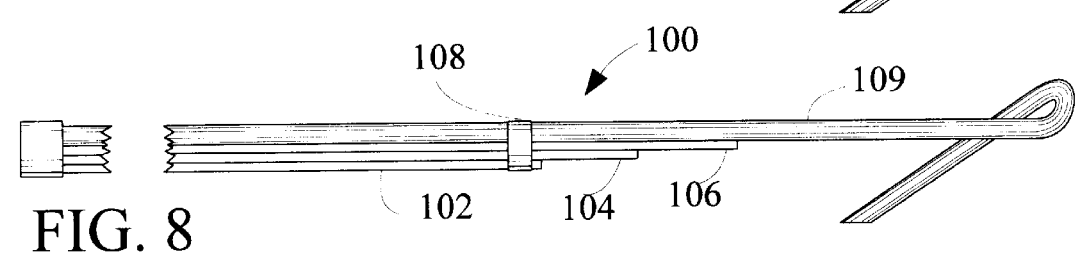
FIG. 8 is a side view of a staggered optical localization fiber.

FIG. 8 illustrates a staggered optical localization fiber bundle 100 with a plurality of staggered optical fibers 102, 104, and 106. A fastener 108 secures a plastic or metallic hook 109.

Figure 9:
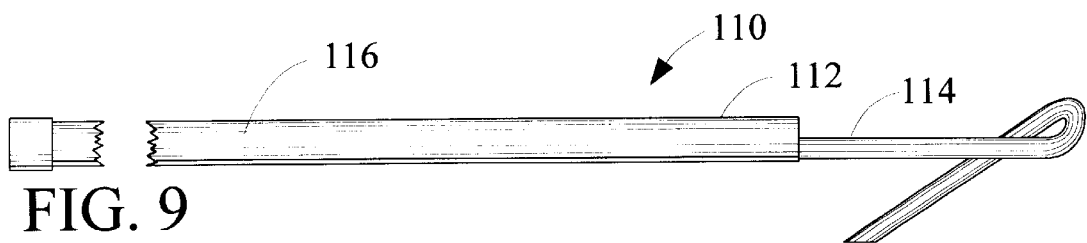
FIG. 9 is a side view of a coated tandem optical localization fiber.

FIG. 9 illustrates a coated tandem hookwire-optical localization fiber 110. No fastener is necessary since the cladding and/or coating 112 holds the wire 114 and shaft 116 together.

Figure 10:
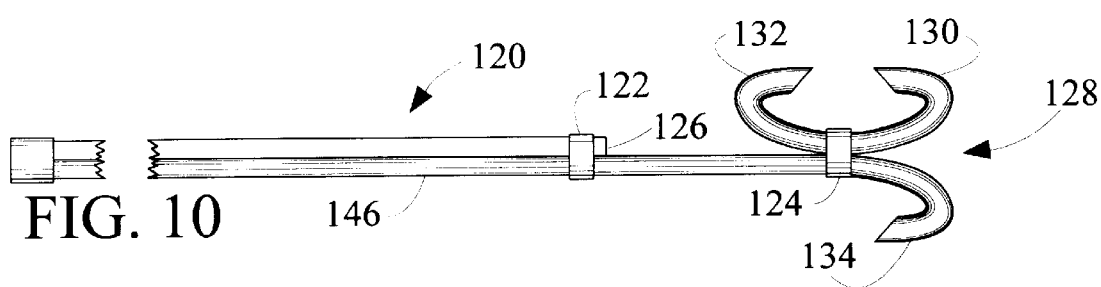
FIG. 10 is a side view of a pincher hook optical localization fiber.

FIG. 10 illustrates a pincher-hook optical localization fiber 120. Fasteners 122 and 124 are positioned at the optical fiber tip 126 and around a triple hook 128 comprising a distal pincher hook 130, a proximal pincher hook 132 and a curved metallic hook 134. Since all hooks have a gentle curve, they may be inserted into the breast localization needle 140 shown in FIG. 11 inside an internal diameter 142 approximately equal to the sum of the diameters of the optical fiber 144 and wire 146. This is illustrated in FIG. 11.

FIG. 11 is an enlarged cross sectional view illustrating the pincher-hook optical localization fiber 120 within the shaft of a needle 140. The needle is inserted into the tissue proximate to the lesion. The fiber optic hook 120 is held in position as the needle 140 is withdrawn thereby releasing the hooks 130, 132, and 134 to engage tissue immobilizing the optical fiber 144.

Figure 12:
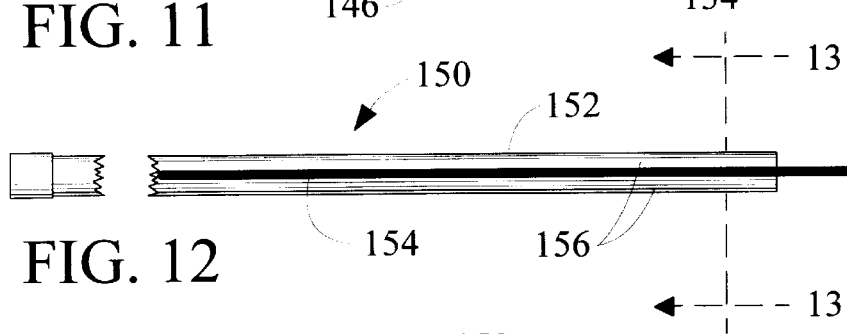
FIG. 12 is a side view of a rosette optical localization fiber bundle with the rear side fibers omitted.

FIG. 12 illustrates a side view of a rosette optical localization fiber bundle 150 with the near side fibers omitted. The bundle also has cladding and/or coating 152, a central wire 154 surrounded by a multiplicity of optical fiber shafts 156 which may be bound to the central wire and each other by adhesive.

Figure 13:
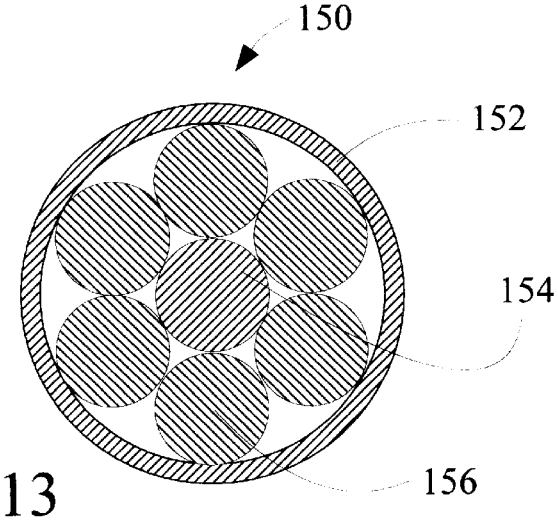
FIG. 13 is a cross sectional view along the line 13—13 with all the optical fibers in place of FIG. 8.

FIG. 13 is an enlarged cross sectional view along line 13—13 of FIG. 12 with the optical fibers in place showing optical fiber shafts 156 arranged in a rosette pattern about the central wire 154. Coating and/or cladding 152 encases the optical fibers and wire.

Figure 14:
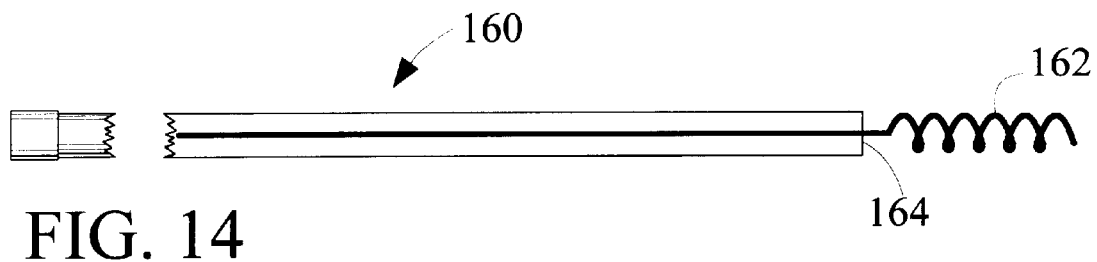
FIG. 14 is a side view of a helical optical localization fiber.

FIG. 14 is a side view of a helical optical localization fiber 160 with a plastic and/or metallic helix 162 at the optical fiber tip 164.

Figure 15:
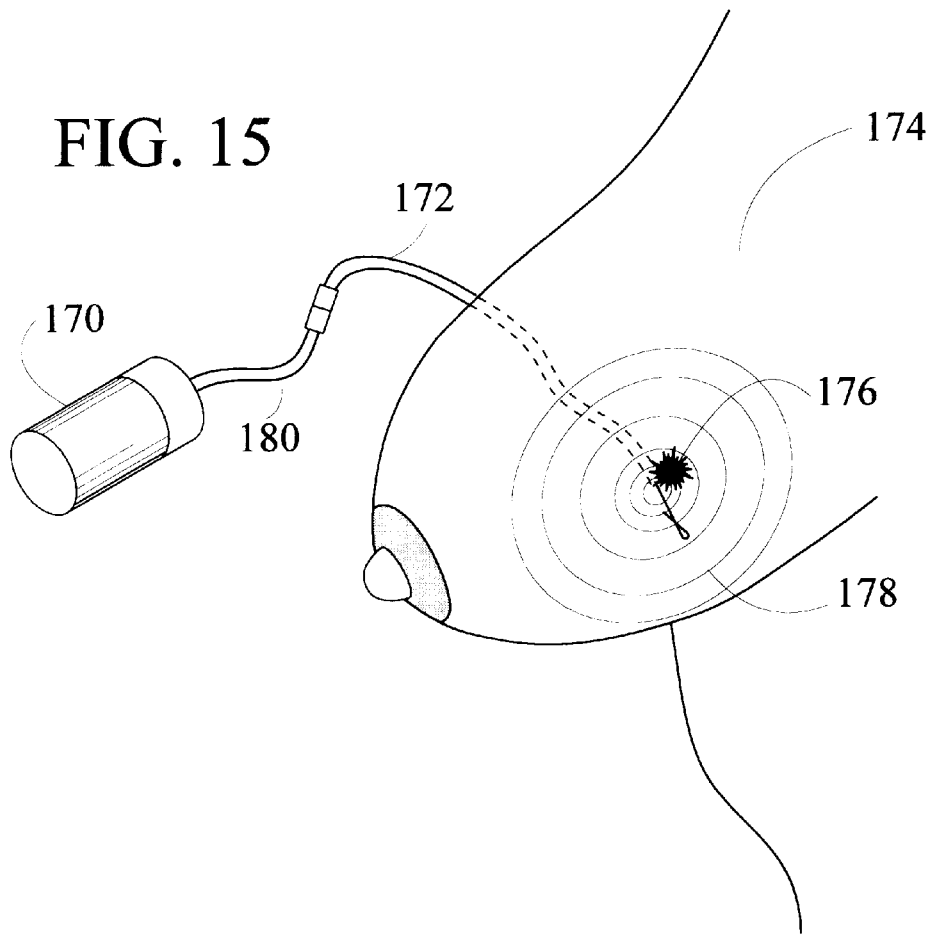
FIG. 15 is a perspective view of a breast with a single composition optical localization fiber hooked proximate to a breast lesion, with light radiating from the tip of the hook.

FIG. 15 demonstrates a laser or other light source 170 coupled to an optical localization fiber 172 within a breast 174 proximate to a lesion 176. The amount of light radiating from the optical fiber tip 178 may be adjusted by changing the laser output. A variety of light sources and wavelengths may be used, such as a high output light emitting diode or a quartz-halogen bulb with a suitable optical fiber connector 180. Pulsed lasers or light sources with a stroboscopic effect may be used to enhance output at the tip 178. The lesion 176 is dark to illustrate powdered carbon which may be injected at the site of the lesion 176. The method of providing medical grade powdered carbon solution in combination with an optical localization fiber for placement at the site of a tissue lesion allows visualization of the lesion, which will be dark because of the carbon, through breast or other tissue as the optical fiber transmits light, In this preferred method of lesion localization, a localizing needle tip is positioned proximate to a lesion via a variety of known stereotactic procedures including x-ray mammography, ultrasound, nuclear medicine or MRI. Approximately 1 cc of a 4% sterile medical grade carbon solution is injected at this location, similar to the known technique of methylene blue injection for preoperative marking of lesions. Although methylene blue diffuses, making it impossible to delay surgery after localization, carbon does not diffuse, and surgery may be scheduled electively following localization.

After the carbon is instilled, the optical localization fiber is passed through the needle 140, and engaged into tissue. The needle is removed, and the localization fiber is left in place. At surgery, a skin incision is made at any desired location. The optical fiber is activated, thus transilluminating the breast. The carbon is identified as a dark spot, surrounded by illuminated tissue, guiding the surgeon to the lesion. The optical localization fiber may be used without carbon, however.

Optical fibers may consist of a bare silica, plastic or glass strand. This strand, or a bundle of strands may function as the core of a coated optical fiber. This coating may be formed from a variety of materials e.g. with silicate or doped silica cladding. Multiple coatings may be formed e.g. a buffer coating external to the cladding. The optical fiber may be designed for single or multiple laser wavelengths and differing peak optical power transmission capability. Numerous types of these optical fibers are available from 3M Corporation of Minneapolis, Minn.

Numerous types of lasers are available for linkage to these optical fibers by those skilled in the art, including diode and Helium-Neon lasers particularly suited to use in the operating room environment. A red beam 650–675 nm at 1 to 20 mW, is easily seen through soft tissue. Other wavelengths and powers may be used, however.

In accordance with the features of the invention all fibers may be inserted through any needle similar in design to those currently employed for breast localization. All fibers may include glass, plastic, silicate or any material capable of electromagnetic wave transmission. All fiber tips may be fabricated of any synthetic, naturally occurring or metallic material, or any combination thereof. All fibers may be supplied with a diffuser tip formed from plastic, glass, quartz, sapphire or other translucent materials. All fibers may connect with a laser of an appropriate wavelength and power, a quartz-halogen light source, a high output light emitting diode, or any other type of light source deemed appropriate by those skilled in the art. All fibers may be linked to these light sources by various optical fiber connectors such as a ferrule connector. All fibers may be clad or unclad with hard or soft cladding along any portion of their length. All fibers may have an external buffer coat. All fibers are sterilizable. All hooks have a spring action for easy passage through a localization needle and engagement into tissue as the localization needle is withdrawn. All embodiments may be used for pre-operative localization of tumors in other body parts such as lung, liver and brain. All embodiments may be used for localizations guided by x-ray mammography, MRI, ultrasonography or nuclear medicine. All embodiments may be used in conjunction with apparatus for characterization of the optical properties of neoplasms.

To appraise the viability of the inventive concepts, both clad and coated and bare optical fiber tips were placed within chicken breast. Light from a 5 mW, 675 nm diode laser was passed down each fiber. Although the amount of light radiating from the bare optical fiber tip decreased when the fiber was surrounded by moist tissue compared with air, the location of the tip of the fiber was well seen through several centimeters of tissue. The clad and coated fiber tips were more easily identified. Injection of carbon through a needle followed by illumination of the tissue by the fiber was performed. The carbon-marked region appeared dark, surrounded by illuminated tissue.

From the foregoing, it should now be recognized that optical localization fiber embodiments have been disclosed herein especially suited for preoperative localization of soft tissue lesions within breast, lung or brain, as well as for lesions within the retroperitoneal cavity and liver. These fibers may be positioned at a chosen location through medical instruments such as probes, cannulas or needles, using x-ray, magnetic resonance, computed tomography, ultrasound or nuclear medicine guidance. The fibers are retained with tissue by a variety of means disclosed herein.

Embodiments in accordance with the invention offer several potential advantages. The approximate location of the lesion may be determined by viewing the light radiating through tissue from the optical fiber tip. The surgeon operating on a localized breast may be able to approach the site of the lesion along the shortest route. This route does not necessarily have to be along the course of the localization wire. Because the site of the lesion can be determined through several centimeters of tissue, smaller dissections may be utilized thereby limiting the amount of cosmetic deformity resulting from a larger dissection. Because no manipulation of a hookwire is necessary either by pulling it or curving along it, the chance of displacement of the hook, and the chance of cutting through the wire are minimized. The continuous visualization of light emanating from the tip of the optical fiber provides the surgeon with continuous feedback, which is not practically obtained through intra-operative fluoroscopy or ultrasonography.

Carbon marking of the lesion or lesion margin facilitates intra-operative localization and excision. The use of optical fibers for breast localization may permit characterization of the optical properties of breast tumors, if a receptive optical fiber is positioned at a chosen location proximate to the tumor and the transmitting optical fiber. In this manner, determination of malignancy versus benignancy is possible prior to engagement of the hook. In addition, carbon marking may be used to determine the presence or absence of the lesion in question within the surgically excised tissue. This is particularly useful if the lesion has been localized by magnetic resonance imaging, and the lesion is not visible on x-ray mammography, since radiographs of the excised specimen may be indeterminate.

The preferred embodiments of the invention described herein are exemplary and any feature, shape, material composition or dimension of any embodiment may be readily combined or altered to achieve an equivalent result, all of which are intended to be embraced within the scope of the appended claims.

What is claimed is:

1. An optical localization fiber comprising:
   an optical fiber for connecting to a light source; and,
   means for retaining the tip of said optical fiber proximate to a chosen location within tissue.

2. The optical localization fiber of claim 1 wherein said retaining means includes a metallic hook.

3. The optical localization fiber of claim 1 wherein said retaining means includes a plastic hook.

4. The optical localization fiber of claim 1 wherein said retaining means includes a braided hook.

5. The optical localization fiber of claim 1 wherein said retaining means includes a helix.

6. The optical localization fiber of claim 1 further including a plurality of optical fibers.

7. The optical localization fiber of claim 1 wherein said retaining means is formed from said optical fiber.

8. The optical localization fiber of claim 1 wherein said retaining means includes a plurality of hooks.

9. The localizer of claim 8 wherein said plurality of hooks includes a triple hook.

10. The optical localization fiber of claim 1 wherein said retaining means includes a longitudinal wire having a hook; and,
    said longitudinal wire and said optical fiber are tandem.

11. The optical localization fiber of claim 10 wherein said optical fiber and said longitudinal wire are coated.

12. The optical localization fiber of claim 1 wherein said optical fiber is bare.

13. The optical localization fiber of claim 1 wherein said optical fiber is coated.

14. The optical localization fiber of claim 1 wherein said optical fiber is clad.

15. The optical localization fiber of claim 1 wherein said optical fiber is bundled.

16. The optical localization fiber of claim 1 further including a diffuser tip.

17. An optical fiber localization system comprising:
    a light source;
    an optical fiber having a tip;
    a connector for connecting said optical fiber to said light source; and,
    means for retaining said tip of said optical fiber within tissue.

18. The optical fiber localization system of claim 17 wherein said light source is a laser.

19. The optical fiber localization system of claim 17 wherein said light source is a light emitting diode.

20. The optical fiber localization system of claim 17 wherein said light source is a light bulb.

21. A method for preoperative localization of a lesion in tissue within a body part, comprising the steps of:
    providing an optical fiber having a fiber tip;
    providing retention means to retain said optical fiber within the tissue;
    imaging the lesion within the body part;
    providing a medical instrument having an instrument tip;
    positioning said instrument tip proximate to the lesion;
    inserting said optical fiber and said retention means through said medical instrument to position said fiber tip proximate to the lesion;
    withdrawing said medical instrument allowing said retention means to retain said fiber tip within the body part;
    providing a light source;
    attaching said optical fiber to said light source causing a light at said fiber tip; and,
    viewing the light radiating through the body part from said fiber tip to determine the approximate location of the lesion.

22. The method of claim 21 further including the step of injecting a solution of medical grade powdered carbon through said medical instrument between said positioning and said inserting steps.

* * * * *